United States Patent [19]

Sugawara et al.

[11] 4,328,211

[45] May 4, 1982

[54] ANTIBIOTIC ACTINOMADURA-L-31 A, B

[75] Inventors: Hideo Sugawara; Yukio Miyazaki; Akio Seino, all of Tokyo, Japan

[73] Assignee: Kaken Chemical Co., Ltd., Tokyo, Japan

[21] Appl. No.: 231,359

[22] Filed: Feb. 4, 1981

[30] Foreign Application Priority Data

Feb. 15, 1980 [JP] Japan .................................. 55-16647

[51] Int. Cl.$^3$ ............................................. A61K 35/00
[52] U.S. Cl. .................................... 424/117; 424/115; 435/169
[58] Field of Search ................. 435/169; 424/117, 115

[56] References Cited

PUBLICATIONS

C.A. 79:103593g (J. Antibiol. 1973, 26(6), 343–350).

*Primary Examiner*—Jerome D. Goldberg
*Attorney, Agent, or Firm*—Oblon, Fisher, Spivak, McClelland & Maier

[57] ABSTRACT

Antibiotic Actinomadura-L-31 A has the characteristics as the hydrochloride salt:
appearance: white or pale yellow powder
melting point: non-clear melting point
specific rotation: $[\alpha]_D^{25}$ −34° (C: 0.5, pH: 7.5 water)
elementary analysis: (found) C: 51.71%; H: 6.23%; O: 21.03%; N: 13.94%; S: 5.82%; Cl: 1.17%
constitutive aminoacids: aspartic acid; glutamic acid; glycin; valine; phenylalanine; histidine; leucine; tryptophan
ultraviolet absorption spectrum: FIG. 1, maximum absorption:
  280 nm: $E_{1\ cm}^{1\%} = 45.2$
  290 nm: shoulder $E_{1\ cm}^{1\%} = 38$
infrared spectrum: FIG. 2, absorption (cm$^{-1}$) 3350, 3050, 2950, 1660, 1530, 1430, 1395, 1340, 1255, 1235, 1100, 745, 700

Antibiotic Actinomadura-L-31 B has the characteristics as the hydrochloride salt:
appearance: white to pale yellow powder
melting point: non-clear melting point
specific rotation: $[\alpha]_D^{25}$ −26° (C: 0.5; pH: 7.5 water)
elementary analysis: (found) C: 51.10%; H: 6.34%; O: 20.75% N: 14.81%; S: 5.91%; Cl: 1.08%
constitutive aminoacids: aspartic acid; threonine; glutamic acid; proline; glycin; valine; phenylalanine; tryptophan
ultraviolet absorption spectrum: FIG. 3, maximum absorption:
  280 nm: $E_{1\ cm}^{1\%} = 44.8$
  290 nm: shoulder $E_{1\ cm}^{1\%} = 37.3$
infrared spectrum: FIG. 4, absorption (cm$^{-1}$) 3350, 3050, 2950, 1660, 1520, 1440, 1390, 1340, 1260, 1230, 1100, 745, 700.

3 Claims, 4 Drawing Figures

ANTIBIOTIC ACTINOMADURA-L-31 A, B

BACKGROUND OF THE INVENTION

1. Field of the Invention

The present invention relates to an antibiotic Actinomadura-L-31 A, B and a preparation thereof. The antibiotic Actinomadura-L-31 A, B are novel sulfur-containing peptide antibiotics.

2. Description of the Prior Arts

Certain sulfur-containing peptide antibiotics have been known. The typical known sulfur-containing peptide antibiotics include Thiopeptin (J. Antibiot 23, 113 (1970)), Thiostrepton (Antibiotics Annual, p 554 (1955/56)), Taitomycin (J. Antibiot, A 12 1, (1959)), Siomycin (J. Antibiot, 22 364 (1969)), Pepthiomycin (J. Antibiot, 21 429 (1968)), Gardimycin (J. Antibiot, 29 501 (1976)), Kobenomycin (J. Antibiot, 21 320 (1968)), Leucinamycin (J. Antibiot, A 20 194 (1967)), Macromomycin (J. Antibiot, 21 44 (1968)), and Neocarzinostatin (J. Antibiot, A 18, 68 (1965)).

SUMMARY OF THE INVENTION

It is an object of the present invention to provide novel Actinomadura-L-31 A, B which are novel antibiotics.

The antibiotic Actinomadura-L-31 A has the characteristics as the hydrochloride salt:
appearance: white or pale yellow powder
melting point: non-clear melting point
specific rotation: $[\alpha]_D^{25} -34°$ (C: 0.5, pH: 7.5 water)
elementary analysis: (found) C: 51.71%; H: 6.23%; O: 21.03%; N: 13.94%; S: 5.82%; Cl: 1.17%
constitutive aminoacids: aspartic acid; glutamic acid; glycine; valine; phenylalanine; histidine; leucine; tryptophan
ultraviolet absorption spectrum: FIG. 1, maximum absorption:
  280 nm: $E_{1\ cm}^{1\%} = 45.2$
  290 nm: shoulder $E_{1\ cm}^{1\%} = 38$
infrared spectrum: FIG. 2, absorption cm$^{-1}$) 3350, 3050, 2950, 1660, 1530, 1430, 1395, 1340, 1255, 1235, 1100, 745, 700
and the antibiotic Actinomadura-L-31 B has the characteristics as the hydrochloride salt:
appearance: white to pale yellow powder
melting point: non-clear melting point
specific rotation: $[\alpha]_D^{25} -26°$ (C: 0.5; pH: 7.5 water)
elementary analysis: (found) C: 51.10%; H: 6.34%; O: 20.75% N: 14.81%; S: 5.91%; Cl: 1.08%
constitutive aminoacids: aspartic acid; threonine; glutamic acid; proline; glycine; valine; phenylalanine; tryptophan
ultraviolet absorption spectrum: FIG. 3, maximum absorption: 280 nm:
  $E_{1\ cm}^{1\%} = 44.8$
  290 nm: shoulder $E_{1\ cm}^{1\%} = 37.3$
infrared spectrum: FIG. 4, absorption (cm$^{-1}$) 3350, 3050, 2950, 1660, 1520, 1440, 1390, 1340, 1260, 1230, 1100, 745, 700

DETAILED DESCRIPTION OF THE PREFERRED EMBODIMENTS

The inventors have found to produce and accumulate antibiotic substances in a cultivation of a microorganism belong to Genus Actinomadura which is isolated by the inventors and have succeeded in the separation of the antibiotic substances.

In view of the physicochemical properties, the antibiotics of the present invention are considered as sulfur-containing peptide antibiotics, however, the antibiotics are different from Thiopeptin, Thiostrepton, Taitomycin, Siomycin, Pepthiomycin, Gardimycin, Kobenomycin, Leucinamycin, Macromomycin and Neocarzinostatin. The antibiotics of the present invention are novel antibiotics referred to as Actinomadura-L-31 which are produced as the mixture of L-31 A and L-31 B.

The antibiotic Actinomadura-L-31 can be produced by culturing L-31 producing microorganism in Genus Actinomadura and separating L-31 from the cultured medium.

The microorganism used for producing Actinomadura-L-31 can be any microorganism in Genus Actinomadura which have L-31 producing function. It is especially preferable to use Actinomadura sp. L-31 strain deposited in Fermentation Research Institute of Japan as FERM-5324 which was newly isolated by the inventors and also deposited as ATCC No. 31793 in American Type Culture Collection.

The microorganism Actinomadura sp. L-31 strain used in the present invention has true substrate mycelium and aerial mycelium and produce a chain of spores but not sporangium nor planospore in its sporophore and has aerobic and mesophilic properties. Diagnostist components of whole cell hydrolysate of Actinomadura sp. L-31 strain contain mes-diaminopimelic acid, 3-o-methyl galactose, and galactose but do not contain L,L-diaminopimelic acid, arabinose and xylose. It is considered that Actinomadura sp. L-31 is a strain in Genus Actinomadura in Order Actinomycetales. Actinomadura sp. L-31 strain has the following characteristics.

(I) Morphological characteristics

The substrate mycelium is well developed and branched and does not form the true spore. The substrate mycelium has a diameter of about 0.5 μm and does not form a zig-zag branched form. The mycelium does not cause fragmentation to be a bacillary or coccoid elements to turbid the liquid medium in the static culture in a liquid medium such as tryptone yeast-extract broth medium at 28° C. for 2 weeks. The aerial mycelium causes adhesion in moderate or higher in starch agar medium, glycerol-calcium malate agar and glucose agasparagine agar plus yeast-extract, to give powdery pale grayish blue in appearance. In the microscopic observation, it has well-developed straight or flexous long axis and short sporophores which are oppositely or alternatively branched, but has not true verticils. The sporophore forms a short chain of spores having 15 or less in a hook, loop or wavy form, but not true spiral form in the above-mentioned agar media or tyrosine agar medium, yeast extract-malt extract agar medium and oatmeal agar medium. The spore has oblong shape and has a size of about 0.8 μm × 1.2 μm and has warty on its surface, has clear boundary, but has not sporangium, pseudosporangium, sclerotium, coremium and planospore.

(II) Cultural characteristics

In accordance with the test described in E. B. Shirling et al. Int. J. Syst. Bacteriol Vol. 16, page 313–340 (1966), the tests are carried out together with the additional known tests with the known media.

The color is determined under the standard light source of xenon lump with Color Harmony Manual Fourth edition (Container Corporation of America, Chicago, 1958) as the color standards. When the corresponding color tab is found, it is shown by the common names, but the common names are not repeated in the repeat description. The color tab code of the color harmony manual is shown in parenthesis.

The following data show growth conditions cultured in each medium at 28° C. for one month otherwise specified.

(1) Sucrose-nitrate agar (Difco-Bacto) medium
Growth: thin, partially slightly good surface: colorless to Lt. Apricot (4 ea) Color is not changed in 0.05 N-HCl aq. or 0.05 N-NaOH aq.
Aerial mycelium: none
Soluble pigment: none (2) Glucose-asparagine agar medium
Growth: moderate, bamboo, buff, straw, wheat (2 fb)
Aerial mycelium: none in naked eye
Soluble pigment: none (3) Glycerol-asparagine agar medium (ISP-5, Difco-Bacto)
Growth: substantially none
Aerial mycelium: none in naked eye
Soluble pigment: none (4) Starch-agar medium (ISP-4 Difco-Bacto)
Growth: moderate substantially colorless
Aerial mycelium: powdery, good, Haze Blue (13 ec)
Soluble pigment: none
Other: remarkably weak hydrolysis of starch: non-soluble of calcium carbonate.

(5) Tyrosine agar medium (ISP-7 Difco-Bacto)
Growth: good: slightly spreading, 4 ea.(non-color change in an acid or a base)
Aerial mycelium: moderate, powdery flesh pink, pale pink, petal pink, shell pink (6 ca)
Soluble pigment: none
Others: none-production of melanoid pigments (6) Nutrient agar medium (Difco-Bacto)
Growth: moderate: cream color
Aerial mycelium: poor dotted: white
Soluble pigment: none (7) Yeast extract-malt extract agar medium (ISP-2 Difco-Bacto)
Growth: moderate-good Lt. Tan (3gc)
Aerial mycelium: good, powdery dusty white
Soluble pigment: none (8) Oatmeal agar medium (ISP-3)
Growth: good, flat spreading, pearl, shell tint (3 ba)
Aerial mycelium: good, powdery, alabaster tint like (13 ba)
Soluble pigment: none (9) Glycerol-calcium malate agar medium
Growth: moderate: flat, ivory like (3 db)
Aerial mycelium: moderate, powdery dusty blue Lt. gray blue, mist blue (16 ge)
Soluble pigment: none
Others: non-soluble of calcium malate

(10) 0.2% Yeast extract added glucose asparagine agar medium
Growth: moderate: camel, maple sugar tan (3 ie) or bluish gray
Aerial mycelium: moderate or good, powdery, claud blue (15 cb)
Soluble pigment: bright brown (III) Physiological and biochemical characteristics (1) Temperature range (0.2% yeast extract added glucose asparagine agar medium; 2 weeks)
   Optimum temperature: 28°–35° C.
   No growth temperature: upper limit 40° C. lower limit 16° C.

(2) Liquefaction of glucose-peptone-gelatine stab (26° C.; one month): positive (3) Hydrolysis of starch (Starch agar medium, ISP-4 I-IK reaction): negative to weak positive (slight)

(4) Coagulation and peptonization of skim milk (37° C.): non-coagulation substantial peptonization (5) Formation of melanine: negative in tryptone-yeast-extract broth, peptone-yeast extract iron agar medium or tyrosine agar medium:
   In melanine-formation agar medium at 28° C. negative after one week, slight positive after two week (reddish brown), positive after three week (brown)

(6) Solubility of xanthine, hypoxanthine, adenine, tyrosine:
   positive: tyrosine, hypoxanthine;
   negative: adenine, xanthine (7) NaCl torelance (Bennett's agar medium+0, 4, 7, 10 13% NaCl)
   growth up to 4%
   none-growth at 7%

(IV) Carbon source utilization (Pridham and Gottlieb's basal agar medium ISP-9, Difco-Bacto; C-2 agar medium)

positive: D-glucose, L-arabinose, D-xylose, L-rhamnose
negative: D-fructose, sucrose, i-inositol, raffinose, D-mannitol, salicin The same results are found regardless of kinds of the basical media and addition or non-addition of vitamins B (0.5 mg. of thiamine-HCl, 0.5 mg. of riboflavin, 0.5 mg. of niacin, 0.5 mg. of pyridoxine-HCl, 0.5 mg. of i-inositol, 0.5 mg. of Ca-pantothenate, 0.5 mg. of PABA and 0.25 mg. of biotin in 1 liter).

(IV) Diagnostic components of whole cell hydrolysate

The diagnostic components contain meso-diaminopimelic acid, 3-O-methyl-D-galactose and galactose but do not contain L,L-diaminopimelic acid, 3-hydroxydiaminopimelic acid, arabinose and xylose.

In the prior arts, the known strains in Genus Actinomadura having taxonomic characteristics include
   *Actinomadura verrucosospora*
   Nonomura and Ohara 1971
   (Hakko Kogaku 49 11, p. 904, 1971)
   *Actinomadura citrea* Lavrova et al., 1972 (ANtibiotiki 17 11, p. 965 1972)
   *Actinomadura coerulea* Preobrazhenskaya et al., 1975 (Antibiotiki 20 5, p. 404 1975)
   *Actinomadura luteofluorescens* (Shinobu) Preobrazhenskaya et al., (Microbiologa 44 p. 524, 1975)

In Actinomycetes and Related Microorganisms 12 1, p. 30, 1977, by Preobrazhenskaya et al., it is described that the color of the aerial mycelium on synthetic media is pink at first and is changed into blue. On the other hand, in International J. Systematic Bacteriology 19, p. 391–512, 1969, it is described that the color of the aerial mycelium on ISP media, is yellow or red series and the color of substrate mycelium is yellow or greenish yellow on yeast extract-malt extract agar medium, and is reddish orange or yellowish pink on the starch agar medium or the glycerol-asparagine agar medium. On the other hand, the color of the growth of Actinomadura sp. L-31 strain is beige color on the former media and is substantially colorless on the latter two media. This is quite different from the formers.

In view of carbon source utilization, the formers utilize D-fructose, sucrose and D-mannitol, whereas Actinomadura sp. L-31 strain does not utilize them. This is one of the difference.

The color of aerial mycelium of Actinomadura citrea is yellow at first and is changed to blue, and the soluble pigment on the synthetic media is yellow. These are different from the Actinomadura sp. L-31.

In *Actinomadura verrucosospora*, the color of substrate mycelium is pink or organge on the starch agar medium and glycerol-asparagine agar medium and light gray aerial mycelium is formed on the starch agar medium and D-fructose and D-mannitol are utilized. This is different from Actinomadura sp. L-31 strain.

*Actinomadura coerulea* can not be identified since it is not deposited.

It is possible to use variation of the strain obtained by certain artificial variations of the Actinomadura sp. L-31 strain by application of ultraviolet rays, X-rays, radioactive rays and a chemical reagent.

The culture can be carried out by the conventional culture method for actinomycetes or the modification thereof. In the industrial culture, it is preferably to carry out the aerobic fermentation in a fermentation tank. The temperature for the culture can be in a range for growthing the microorganism to form the Actinomadura-L-31 and is usually in a range of 25° to 35° C.

The media for the culture can be prepared by using substances used for the culture of actinomycetes. The carbon source can be glucose, dextrin, starch etc. The nitrogen source can be wheat germ, soybean powder, corn steep liquor, meat extract and ammonium sulfate. The inorganic salt such as sodium, potassium or calcium salt can be incorporated. It is preferable to control pH for the culture such as 5 to 9. It is preferable that the medium for the culture preferably comprises 0.5 to 20% W/V of the carbon source and 0.5 to 10% W/V of the nitrogen source.

The time for culture is depending upon the condition and is usually 3 to 8 days. The Actinomadura-L-31 is included in the mycelia and filtrate. Depending upon the condition of the culture and the kind of the strain, the Actinomadura-L-31 A and L-31 B can be formed at various ratios.

In order to separate and purify the Actinomadura-L-31 from the cultured product, the conventional methods can be selected and combined in view of the physicochemical properties of the product, for example, the extraction methods with various organic solvents, the phase transfer, or the absorbent or partition chromatography can be combined as desired.

The antibiotic Actinomadura-L-31 formed in the cultured product can be preferably separated as follows.

An organic solvent such as methanol, ethanol and acetone is added to the cultured product to extract the Actinomadura-L-31. The mycelia are separated by a filtration and the filtrate is adjusted to pH of 2 to 3 and then the Actinomadura-L-31 is extracted with said organic solvent. In the same method, the Actinomadura-L-31 can be extracted from mycelia.

The extracted solution is treated by a solvent distillation, a phase transfer, a reextraction, a precipitation or a concentration to dryness etc. to separate a mixture of Actinomadura-L-31 A and L-31 B. The mixture is treated by a chromatography on as suitable solvent such as butanol-acetic acid-water to collect the fraction which imparts antibiotic activity to *Bacillus stearothermophilus* and the fraction is concentrated under a reduced pressure and is further treated if necessary to obtain pure Actinomadura-L-31 A and L-31 B. The Actinomadura-L-31 A and L-31 B are weak acidic compounds which can be separated in a free form and can be separated in a form of sodium or potassium salt or hydrochloride or sulfate form.

The Actinomadura-L-31 A and L-31 B of the present invention have antibiotic activities and are effective as antibiotics or the starting materials thereof. Even though an antibiotic activity is found in a plate test, excellent protective effect is found in a test for infection of *Eschierichia coli* etc. to mice.

The present invention will be further illustrated by certain examples.

EXAMPLE 1

Into 70 ml. of a liquid medium containing 1% of glycerin, 1% of glucose, 1% of starch, 1% of wheat germ, 0.5% of NZ-amine, 0.2% of bear yeast, 0.5% of corn steep liquor, and 0.2% of calcium carbonate, Actinomadura sp. L-31 strain (FERM-5324) was inoculated to culture by a shaking culture method at 28° C. for 5 days to prepared a preculture solution.

Into a 200 liter fermation tank, 100 liter of a liquid medium containing 2% of glycerin, 2% of glucose, 2% of starch, 1% of wheat germ, 0.5% of NZ-amine, 0.2% of beer yeast, 0.5% of corn steep liquor and 0.2% of calcium carbonate was charged and 1 liter of said preculture solution was inoculated to culture them to 28° C. for 6 days under the condition of an air bubbling rate of 100 liter/min. and a revolutional number per minute of 250 r.p.m.

After the culture, the cultured product was controlled to give pH of 2 with HCl and 2% of diatomaceous earth was added to the cultured product and filtered. An extraction of the product was carried out by adding equal volume of butanol to 80 liter of the filtrate. On the other hand, the mycelia are extracted with 80 liter of 80% acetone-water solvent. After distilling off acetone, the water phase was extracted with butanol. The extracted butanol was combined with the solvent phase obtained from the culture filtrate and the mixture was concentrated in a reduced pressure. The concentrated solution was admixed with 10 liter of ethyl acetate to form a precipitate was filtered and dried under a reduced pressure to obtain 50 g. of a crude powder of mixture of Actinomadura-L-31 A and L-31 B.

Into a small amount of a mixed solvent of butanol-acetic acid—water (4:1:1), 2 g. of the crude powder was dissolved and a cellulose column chromatography was carried out with said mixed solvent whereby Actinomadura-L-31 B was firstly eluted and then, L-31 A was eluted.

The fractions were collected and concentrated under a reduced pressure and the residue was dissolved in 300 ml. of butanol and then 300 ml. of 1% sodium bicarbonate was added to carry out the phase separation. The water phase was acidified with hydrochloric acid to give pH of 1.5 to 2.0 and the product was extracted with the same volume of butanol. The butanol layer was washed with water and dried under a reduced pressure to obtain pure Actinomadura-L-31 A (15 mg.) and L-31 B (18 mg.) as hydrochloride salts in a powdery form.

EXAMPLE 2

In accordance with the process of Example 1, the culture was carried out and the cultured product was separated into the mycelia and the filtrate. The mycelia were treated by the process of Example 1 to obtain a concentrated butanol extract solution. On the other hand, the filtrate was adsorbed on about 3 liter of Diaion HP-20 (manufactured by Mitsubishi Chemical Ind. Ltd.) and the adsorbed carrier was washed with water and then 3 liter of 50% methanol-water. The product was extracted with 5 liters of 70% of acetone-water having pH of 2 to 3 to collect the active fraction and the fraction was concentrated under a reduced pressure. The concentrated solution was mixed with 10 liters of butanol to extract the product and the butanol solution was mixed with 5 liters of the butanol extract solution.

The butanol solution was mixed with 5 liters of 1% sodium bicarbonate to carry out the phase separation. The water phase was acidified with hydrochloric acid to give pH of 2 to 3 and the product was extracted with 5 liters of butanol. The butanol extract solution was washed with water and concentrated to dryness under a reduced pressure to obtain about 30 g. of a crude mixture of Actinomadura-L-31 A and L-31 B in a powdery form.

In accordance with the process of Example 1, 2 g. of the crude mixture was purified by a cellulose chromatography to obtain pure Actinomadura-L-31 A (18 mg.) and L-31 B (20 mg.) as hydrochloride salts in a powdery form.

The antibiotic Actinomadura-L-31 A and L-31 B have the following physicochemical properties.

Actinomadura-L-31 A (hydrochloride)

(1) Appearance: white or pale yellow powder
(2) Melting point: non-clear melting point
(3) Specific rotation: $[\alpha]_D^{25} -34°$ (C: 0.5; pH: 7.5 water)
(4) Solubility: soluble to methanol, ethanol, propanol, butanol, acetic acid and dimethylformamide: insoluble to ethyl acetate, chloroform, ether, hexane and water
(5) Stability: relatively stable at pH of 2 to 8
(6) Color reaction: positive to potassium permanganate, ninhydrin and Ehrlinch's reaction: negative to ferric chloride reaction
(7) Elementary analysis: C: 51.71%; H: 6.23%; O: 21.03%; N: 13.94%; S: 5.82%; Cl: 1.17%
(8) Ultraviolet absorption spectrum:
FIG. 1 measured in methanol
maximum absorption:
280 nm ($E_1$ $_{cm}^{1\%}$ = 45.2)
290 nm (shoulder $E_1$ $_{cm}^{1\%}$ = 38)
(9) Infrared spectrum:
FIG. 2 measured by KBr method
absorption (cm$^{-1}$) 3350, 3050, 2950, 1660, 1530, 1430, 1395, 1340, 1255, 1235, 1100, 745, 700
(10) Silica gel thin layer chromatography Rf value:

| Solvent | Rf value |
| --- | --- |
| water saturated butanol | 0.0 |
| butanol: acetic acid: water (2:1:1) | 0.6 |
| butanol: acetic acid: water (4:1:1) | 0.2 |

(11) Constitutive aminoacids:
(a) Before the analysis, the product is hydrolyzed with 6 N-HCl at 110° C. for 17 hours. aspartic acid; glutamic acid; glycine; valine; leucine; phenylalanine; histidine other two unknown aminoacids.
(b) Analysis by ultraviolet spectrum: tryptophan
(12) Antimicrobial spectrum:
Growth inhibition diameters measured by the plate method are shown in Table 1

Actinomadura-L-31 B (hydrochloride)

(1) Appearance: white or pale yellow
(2) Melting point: non-clear melting point
(3) Specific rotation: $[\alpha]_D^{25} -26°$ (C: 0.5; pH: 7.5; water)
(4) Solubility: soluble to methanol, ethanol, propanol, butanol, acetic acid and dimethylformamide: insoluble to ethyl acetate, chloroform, ether, hexane, and water
(5) Stability: relatively stable at pH of 2 to 8
(6) Color reaction: positive to potassium permanganate, ninhydrin and Ehrlich's reaction; negative to ferric chloride reaction
(7) Elementary analysis: C: 51.10%; H: 6.34%; O: 20.75%; N: 14.81%; S: 5.91%; Cl: 1.08%
(8) Ultraviolet absorption spectrum:
FIG. 3 measured in methanol
maximum absorption:
280 nm ($E_1$ $_{cm}^{1\%}$ = 44.8)
290 nm (shoulder $E_1$ $_{cm}^{1\%}$ = 37.3)
(9) Infrared spectrum:
FIG. 2 measured by KBr method
absorption (cm$^{-1}$) 3350, 3050, 2950, 1660, 1520, 1440, 1390, 1340, 1260, 1230, 1100, 745, 700
(10) Silica gel thin layer chromatography

| Solvent | Rf value |
| --- | --- |
| water saturated butanol | 0.0 |
| butanol: acetic acid: water (2:1:1) | 0.7 |
| butanol: acetic acid: water (4:1:1) | 0.5 |

(11) Constitutive aminoacids:
(a) Before the analysis, the product is hydrolyzed with 6 N-HCl at 110° C. for 17 hours. aspartic acid; threonine; glutamic acid; proline; glycine; valine; phenylalanine; other two unknown aminoacids.
(b) Analysis by ultraviolet spectrum: tryptophan
(12) Antimicrobial spectrum:
Growth inhibition diameters measured by the plate method are shown in Table 1.

TABLE 1

| | Antimicrobial spectrum: Growth inhibition diameter (mm) | | | |
|---|---|---|---|---|
| | L-31A | | L-31B | |
| Microbial strain | 500 γ/ml | 125 γ/ml | 500 γ/ml | 125 γ/ml |
| Bacillus stearothermophilus subsp. calidolactis C-953 | 21 | 15 | 23 | 17 |
| Bacillus subtilis PCI 219 | 0 | 0 | 0 | 0 |
| Escherichia coli NIHJ JC$_2$ | 0 | 0 | 0 | 0 |

(13) Even though the growth inhibition effect was not found by the plate method, the protective effect to livings was found. For example, the infection of *Escherichia coli* to mice was prevented at a rate of 40 to 80% and 50 to 100% by intraperitoneal injection of Actinomadura-L-31 A and L-31B at a dose of 50 to 100 mg. to mice.

Bacterial infection tests

Ten of ICR/JCL female mice (5 week age) were used as one group, and each drug was administered by routes of intraperitoneal injection (i.p.) at a dose of 50 mg./kg. per mouse in the case of Actinomadura-L-31 A and 25 mg./kg. per mouse in the case of Actinomadura-L-31 B, three days before the inoculation of the bacteria. Seven days after the inoculation, the non-mortal number of mice was observed. The result is shown in Table 2.

TABLE 2

| Organism | Dose (cells/mouse) | Compound | Non-mortal number |
|---|---|---|---|
| Staphylococcus aureus EQP | 5 × 10$^8$ | L-31 A, 50 mg/kg | 4/10 |
| | | L-31 B, 25 mg/kg | 6/10 |
| | | None | 0/10 |
| Escherichia coli ML-4707 | 5 × 10$^7$ | L-31 A, 50 mg/kg | 5/10 |
| | | L-31 B, 25 mg/kg | 7/10 |
| | | None | 0/10 |
| Pseudomonas aeruginosa IFO-2901 | 2 × 10$^7$ | L-31 A, 50 mg/kg | 7/10 |
| | | L-31 B, 25 mg/kg | 8/10 |
| | | None | 0/10 |
| Proteus mirabilia CCM-680 | 5 × 10$^7$ | L-31 A, 50 mg/kg | 6/10 |
| | | L-31 B, 25 mg/kg | 7/10 |
| | | None | 0/10 |

(14) Test: Acute toxicity:

In the measurement of LD$_{50}$, ICR/JCL female mice (5 week age) (weight 22.0±1.0 g.) were used and the drug was administered by route of intraperitoneal injection and the results were observed after 1 week. LD$_{50}$ was more than 300 mg/kg of Actinomadura-L-31 A and 150–250 mg./kg. of Actinomadura-L-31 B.

Figure 1:
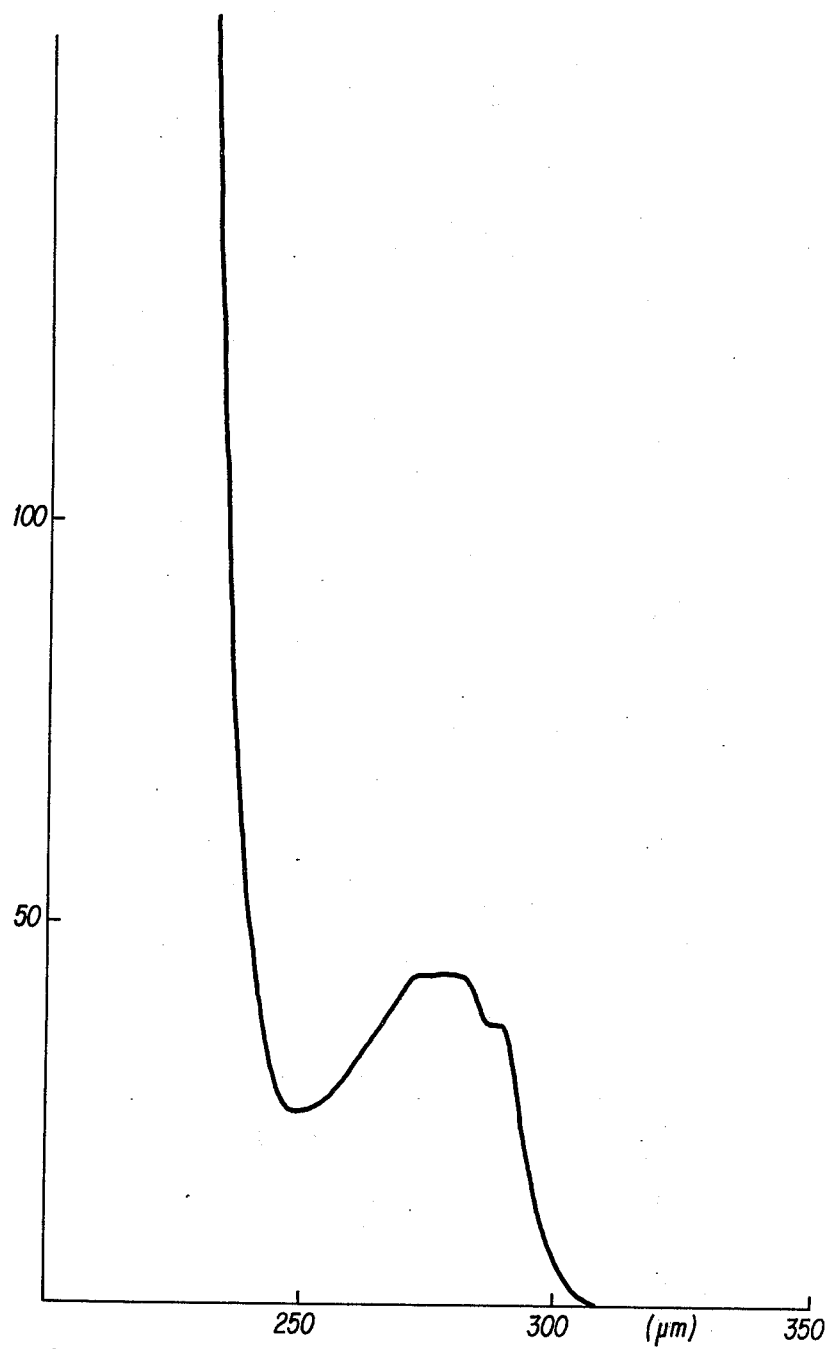
FIG. 1 is the ultraviolet absorption spectrum of Actinomadura-L-31 A.
Figure 2:
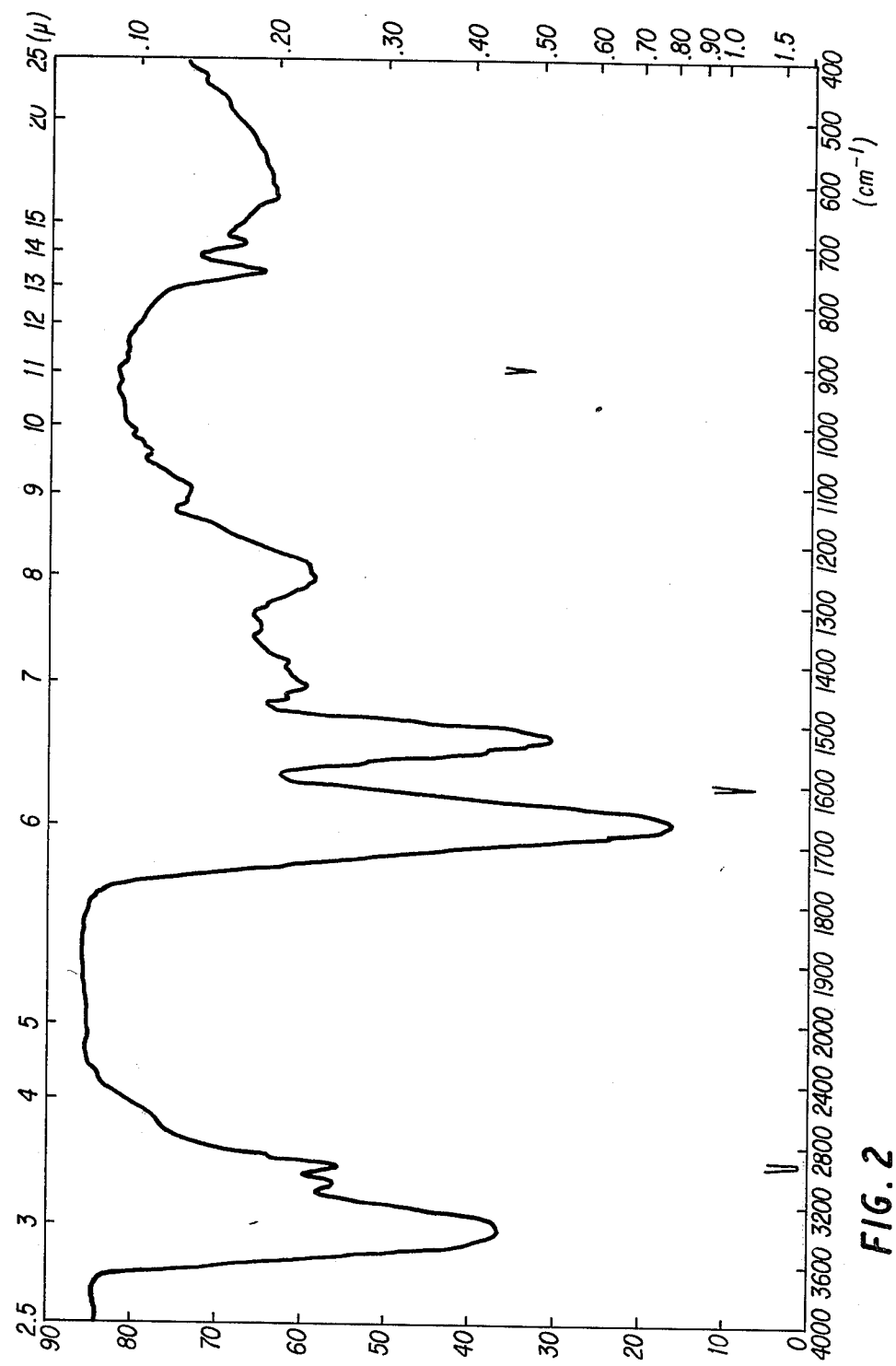
FIG 2 is the infrared spectrum of Actinomadura-L-31 A measured by KBr-Disk method.

We claim:

1. Antibiotic Actinomadura-L-31 A having the characteristics as the hydrochloride salt:

appearance: white or pale yellow powder melting point: non-clear melting point specific rotation: $[\alpha]_D^{25} - 34°$ (C: 0.5, pH: 7.5 water)

elementary analysis: (found) C: 51.71%; H: 6.23%; O: 21.03%; N: 13.94%; S: 5.82%; Cl: 1.17% constitutive aminoacids: aspartic acid; glutamic acid; glycin; valine; phenylalanine; histidine; leucine; tryptophan ultraviolet absorption spectrum: FIG. 1, maximum absorption:

280 nm: $E_1\ _{cm}^{1\%} = 45.2$ 290 nm: shoulder $E_1\ _{cm}^{1\%} = 38$ infrared spectrum: FIG. 2, absorption (cm$^{-1}$) 3350, 3050, 2950, 1660, 1530, 1430, 1395, 1340, 1255, 1235, 1100, 745, 700.

Figure 3:
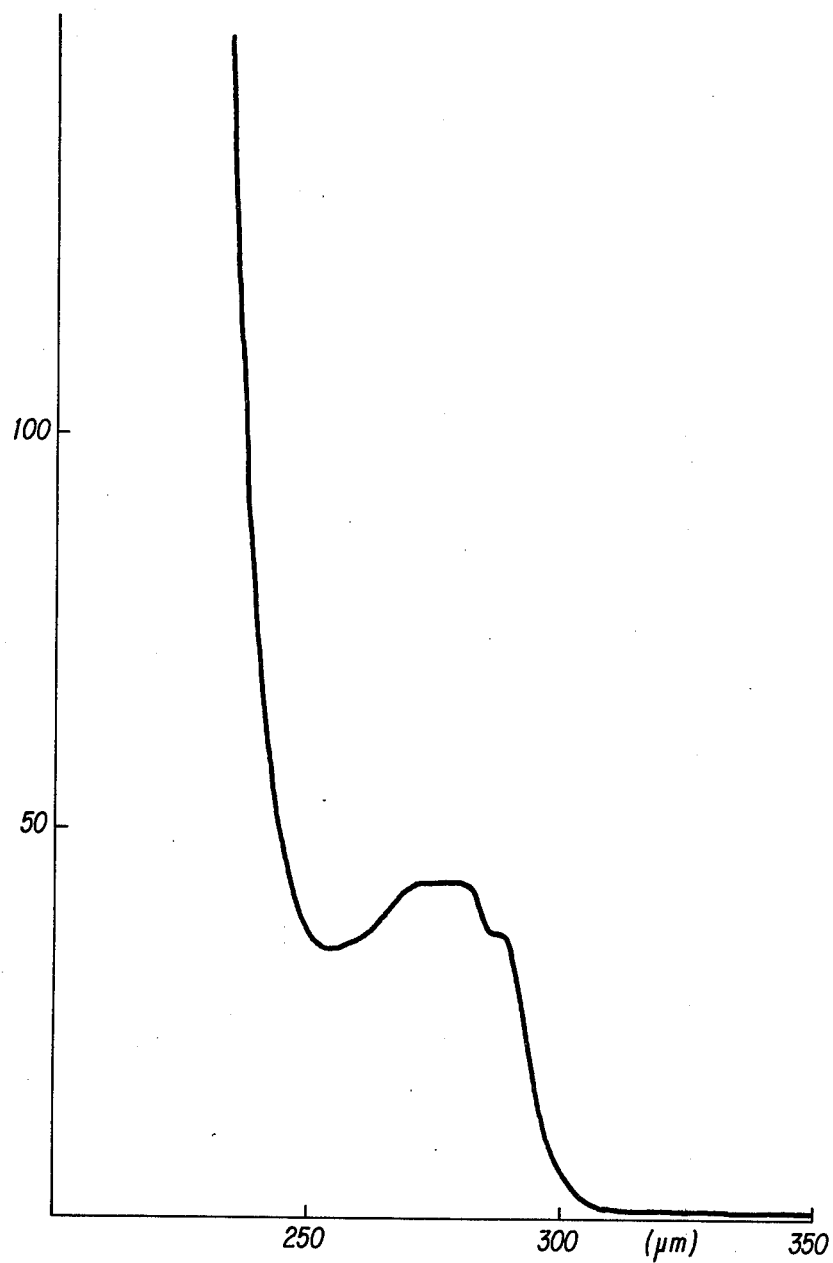
FIG. 3 is the ultraviolet absorption spectrum of Actinomadura-L-31 B.
Figure 4:
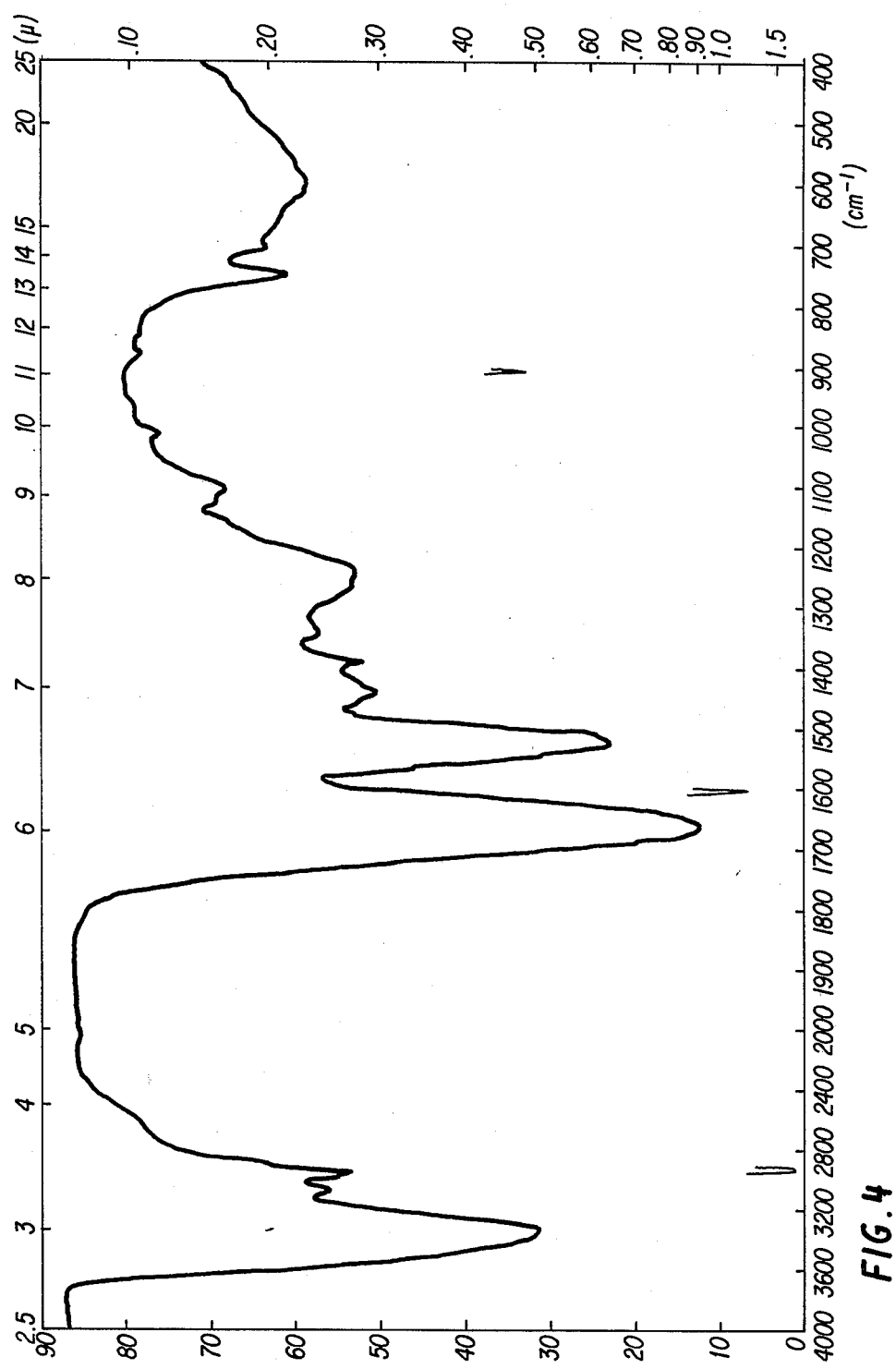
FIG. 4 is the infrared spectrum of Actinomadura-L-31 B measured by KBr-Disk method.

2. Antibiotic Actinomadura-L-31 B having the characteristics as the hydrochloride salt:

appearance: white to pale yellow powder melting point: non-clear melting point specific rotation: $[\alpha]_D^{25} - 26°$ (C: 0.5; pH: 7.5 water)

elementary analysis: (found) C: 51.10%; H: 6.34%; O: 20.75% N: 14.81%; S: 5.91%; Cl: 1.08% constitutive aminoacids: aspartic acid; threonine; glutamic acid; proline; glycin; valine; phenylalanine; tryptophan ultraviolet absorption spectrum: FIG. 3, maximum absorption 280 $E_1\ _{cm}^{1\%} = 44.8$ 290 nm: shoulder $E_1\ _{cm}^{1\%} = 37.3$ infrared spectrum: FIG. 4, absorption (cm$^{-1}$) 3350, 3050, 2950, 1660, 1520, 1440, 1390, 1340, 1260, 1230, 1100, 745, 700.

3. Antibiotic Actinomadura-L-31 comprising Actinomadura-L-31A and L-31B prepared by culturing L-31 producing microorganism of the genus Actinomadura, ATCC No. 31793, in conventional actinomycetes culture medium until the mixture of Actinomadura-L-31A and L-31B is obtained.

* * * * *